United States Patent [19]

Berkovits et al.

[11] 4,421,114

[45] Dec. 20, 1983

[54] TACHYCARDIA TREATMENT

[76] Inventors: Barouh V. Berkovits, 179 Woodcliff Rd., Newton Highlands, Mass. 02161; Ray S. McDonald, 2241 Marion St., St. Paul, Minn. 55113

[21] Appl. No.: 177,285

[22] Filed: Aug. 11, 1980

Related U.S. Application Data

[63] Continuation of Ser. No. 956,191, Oct. 30, 1978, abandoned.

[51] Int. Cl.³ .............................................. A61N 1/36
[52] U.S. Cl. .............................................. 128/419 PG
[58] Field of Search ..... 128/419 D, 419 PG, 703-705

[56] References Cited

U.S. PATENT DOCUMENTS

| | | | |
|---|---|---|---|
| 3,552,386 | 1/1971 | Horth | 128/703 |
| 3,587,563 | 6/1971 | Ragsdole | 128/705 |
| 3,661,158 | 5/1972 | Berkovits | 128/419 PG |
| 4,181,133 | 1/1980 | Kolenik et al. | 128/419 PG |

*Primary Examiner*—William E. Kamm

*Attorney, Agent, or Firm*—Merchant, Gould, Smith, Edell, Welter & Schmidt

[57] ABSTRACT

Treatment of re-entry tachycardias through the use of a pacemaker which includes sequentially timed oscillators for delivering stimulating pulses to an atrium and ventricle, preferably on a demand basis, and a circuit for detecting a tachycardia condition and switching to an asynchronous mode of operation. The detector does not respond to a single extraneous or premature beat, but after a predetermined number of beats occurring above a predetermined normal beat rate the detector switches the pacemaker to an asynchronous mode. Relative variation in the phase of the asynchronous pacing and the tachycardia beats results within a short time in occurrence of a pulse in the critical time period to stop the tachycardia. The use of sequential stimulation in both chambers overcomes some of the problems in selecting the proper site for stimulation. Hysteresis is provided in the heartbeat rate detecting circuit for preventing premature discontinuance of the asynchronous mode due to masking of pulses by the refractory period of the QRS-wave amplifying circuits.

6 Claims, 2 Drawing Figures

TACHYCARDIA TREATMENT

This is a continuation of application Ser. No. 956,191, filed Oct. 30, 1978 now abandoned.

BACKGROUND OF THE INVENTION

Implantable pacemakers have achieved some success in the treatment of tachycardias. Since the primary function of most pacemakers is to maintain the heart rate at or above a minimum value, different circuitry or different modes of operation are usually required for the treatment of tachycardias. Generally speaking, two modes of operation have been proposed: the use of bursts of high frequency pulses, and the use of asynchronous, or fixed rate, pacing.

One way in which re-entry tachycardias may commence is when an atrial premature impulse conducted normally to the ventricle is then able to re-enter the supraventricular region by retrograde conduction via an accessory pathway and cause another atrial depolarization. Continuing repetition of the cycle around this re-entry loop results in a reciprocal rhythm. Interruption of this rhythm can be achieved by a properly timed premature best interferring with the impulse propagation in the re-entry loop. Circulation of the re-entry impulse will then stop because refractory tissue will be encountered in the re-entry pathway. If the pacemaker can apply the properly timed impulse through an electrode having access to the re-entry circuit, refractoryness of tissue can be created ahead of the circulating impulse, thus breaking the tachycardia repetitive cycle. Usually there is only a short time interval in each cycle, a narrow time window, during which a premature beat is effective in terminating the tachycardia.

One prior art technique is to provide a pacemaker that delivers a burst of high frequency pulses during a predetermined time interval following a beat to blanket the critical time window and thus to provide the necessary pulse to break the tachycardia cycle. Although this technique is successful in many cases, it unfortunately cannot be used with some classes of patients to whom the pulse burst might be harmful.

Other prior art techniques have used a demand type pacemaker which is switched into a fixed rate, or asynchronous mode, to treat the tachycardia. In an asynchronous mode, the varying phase relationship between the stimulating pulses and the tachycardia beats is such that within a short period of time an asynchronous pulse will occur at the critical time to interrupt the tachycardia, following which normal demand pacing can be resumed.

One method of treatment of tachycardias by asynchronous pacing involves the use of an implanted demand type pacemaker which can be switched to asynchronous operation by placing an external magnet over the unit. This technique is obviously of limited utility since it depends upon the patient to recognize the tachycardia and initiate the treatment, and there is a risk that the patient may be incapacitated when the tachycardia occurs. Another technique involves the use of an implanted demand pacemaker having circuits to sense a tachycardia rhythm and then automatically revert to fixed rate pacing for the duration of the tachycardia. While this technique has proved useful, potential problems still exist in several areas. Selection of the site within the heart for placement of the electrodes may present a problem in some cases, and unwanted reversion to fixed rate pacing upon occurrence of a single, or a small number of premature beats can also present problems.

SUMMARY OF THE INVENTION

To overcome these and other problems the present invention provides a heart pacemaker for treatment of tachycardia including terminals for connection to a patient's heart for delivery of atrial and ventricular stimulation to the respective chambers thereof, generating means for delivering sequential atrial and ventricular electrical stimulations pulse to the terminals on a recurring basis in an asynchronous mode of operation, and tachycardia detection and control means for sensing beating of the patient's heart and operative to enable delivery of the pulses in the asynchronous mode of operation in response to a heart beat rate greater than a predetermined value.

According to another aspect of the invention, means are provided for detecting a tachycardia condition to enable asynchronous operation, based upon the occurrence of a predetermined number of heart beats having escape intervals of less than a predetermined duration.

According to another aspect of the invention, switching hysteresis is provided in a tachycardia detection and control so as to require a longer sensed escape interval for switching out of asynchronous mode than for switching into asynchronous mode, to compensate for possible masking of detected beats due to the refractory or insensitive period of the heart beat detection filters or amplifiers.

DETAILED DESCRIPTION OF THE PREFERRED EMBODIMENT

Figure 1:
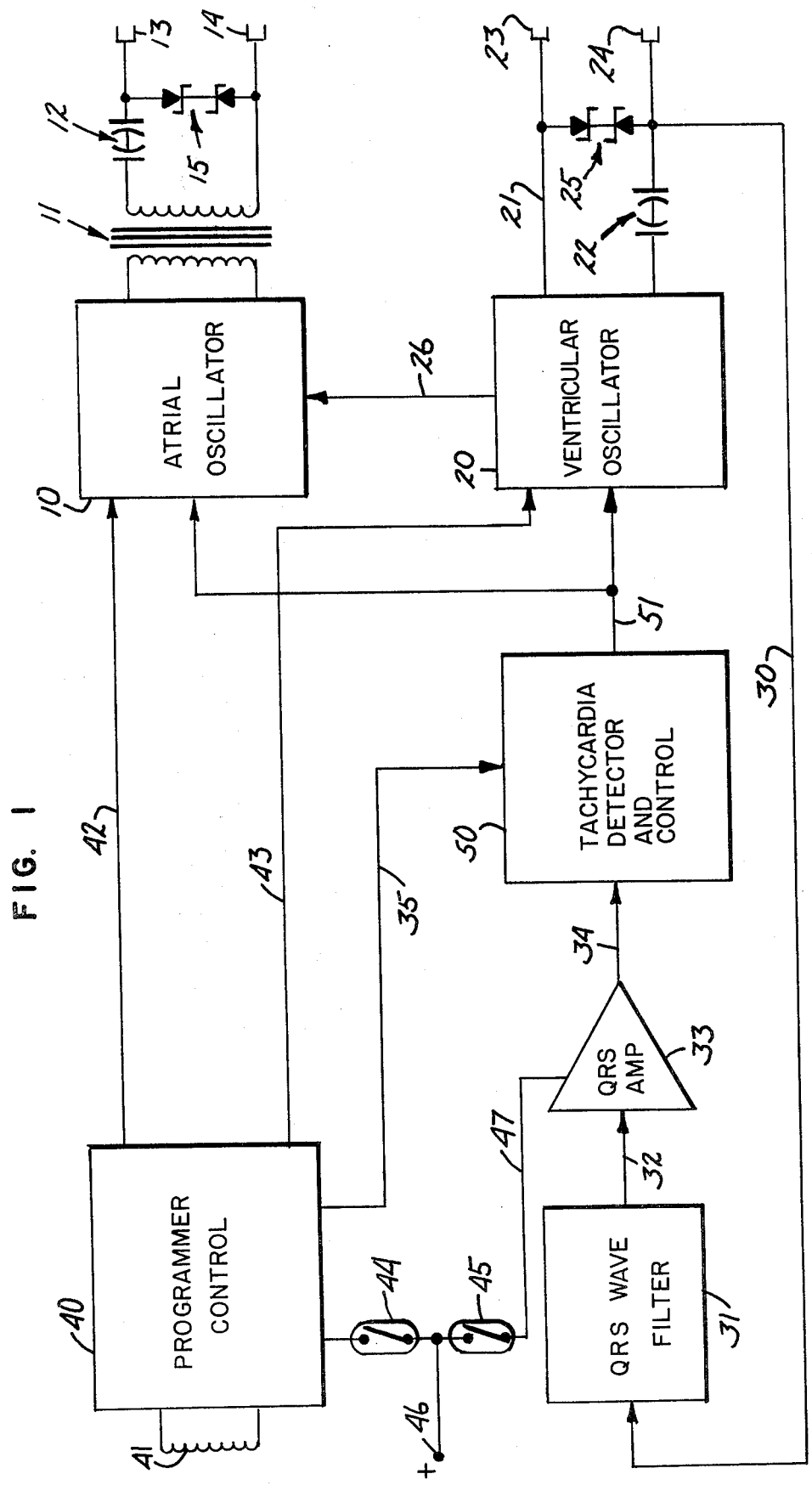
FIG. 1 is a block diagram showing the construction of a pacemaker incorporating the present invention.

FIG. 1 shows in block diagram form a dual-demand atrial-ventricular sequential pacemaker according to the present invention. Reference number 10 designates the atrial oscillator circuit and reference number 20 designates the ventricular oscillator circuit. These oscillators or pulse generating circuits are designed as is generally known in the prior art to produce electrical stimulating pulses, in sequential time relationship, for stimulating the upper and lower heart chambers, respectively. Oscillator 10 generates pulses and delivers them through transformer 11 and coupling capacitors 12 to terminals 13 and 14. Electrode bearing leads, not shown, as are generally known in the art would be provided in use to connect terminals 13 and 14 to the atrium of the heart. Diodes 15 are provided for circuit protection in the event of exposure to defibrillation currents.

Oscillator 20 provides output pulses to terminals 23 and 24, via leads 21 and coupling capacitors 22. Protection diodes 25 are also provided. In use, electrode bearing leads as are generally known in the art would be provided to connect terminals 23 and 24 to the ventrical of the heart.

Terminal 24 is also used for impulse sensing for demand and tachycardia purposes, and it is connected by a signal conductor 30 to a wave filter 31. Wave filter 31 is designed to respond to the QRS-complex of the electrocardiogram which indicates ventricular depolarization, and to pass signals representative thereof, while suppressing the T-wave portion of the electrocardiogram. As a practical matter, it also responds to the ventricular oscillator output pulses even though they are outside the normal frequency band of the filter, since these pulses may be 60 db or more stronger than the heart signals. The output of filter 31 connects via conductor 32 to the input of the QRS amplifier 33. While filter 31 and amplifier 33 are shown as separate blocks for illustrative purposes in FIG. 1, it will be appreciated that the two functions might be combined in a single circuit including active filters. The design of QRS wave filters and amplifiers is generally known in the art, and the specific circuit is not critical to the present invention so long as reasonable efficiency is achieved, and so long as the refractory period of the filter or amplifier is known and preferably made reasonably short as explained more fully hereinafter.

The output of amplifier 33 connects via conductor 34 to the input of circuit 50, which represents the tachycardia detector and control. The preferred circuit and operation of control 50 is described more fully hereinafter with reference to FIG. 2. As seen in FIG. 1, control 50 also receives an input via conductor 35, and provides an output on conductor 51. Conductor 51 connects to both the atrial oscillator 10 and the ventriculator oscillator 20 and serves to control resetting thereof in the demand mode of operation. Conductor 26 connects from oscillator 20 to oscillator 10 for resetting the atrial oscillator following delivery of a ventriculator stimulating pulse, so as to maintain proper synchrony of the A-V stimulation, as is generally known in the art.

Also shown in FIG. 1 is a programmer control 40. Control 40 has an RF antenna or pick-up coil 41 for receiving external programming signals, and it has a plurality of outputs for programming the rates, timings and modes of operation of the device. Conductor 35 from control 40 provides the enable signal to the tachycardia detector and control 50 as is explained more fully below, to enable or disable the dual demand function. Conductors 42 and 43 each represent a plurality of outputs for programming the desired time constants for oscillators 10 and 20. The construction and operation of programmer control 40 and the manner in which it controls the timing of oscillators 10 and 20 is disclosed more fully in our co-pending patent application Ser. No. 874,532 filed Feb. 2, 1978 and assigned to the assignee of the present invention.

Magnetic reed switches 44 and 45 are also preferably provided for actuation by an external magnet which may be placed over the implanted pacemaker, in the manner which is generally known in the prior art. Switch 44 is normally open, and connects from the plus battery terminal 46 to programmer control 40 to permit operation of the programmer while the magnet is in place. Reed switch 45 is normally open and upon closure disables QRS amplifier 33 via conductor 47. Actuation of switch 45 by the external magnetic field disables amplifier 33 and the normal demand function of the pacemaker, to permit testing thereof after implantation, as is generally known in the prior art. It will be appreciated that conductors are also provided for supplying power from the pacemaker's battery to the other circuits, but these have been omitted from FIG. 1 for purposes of clarity.

Figure 2:
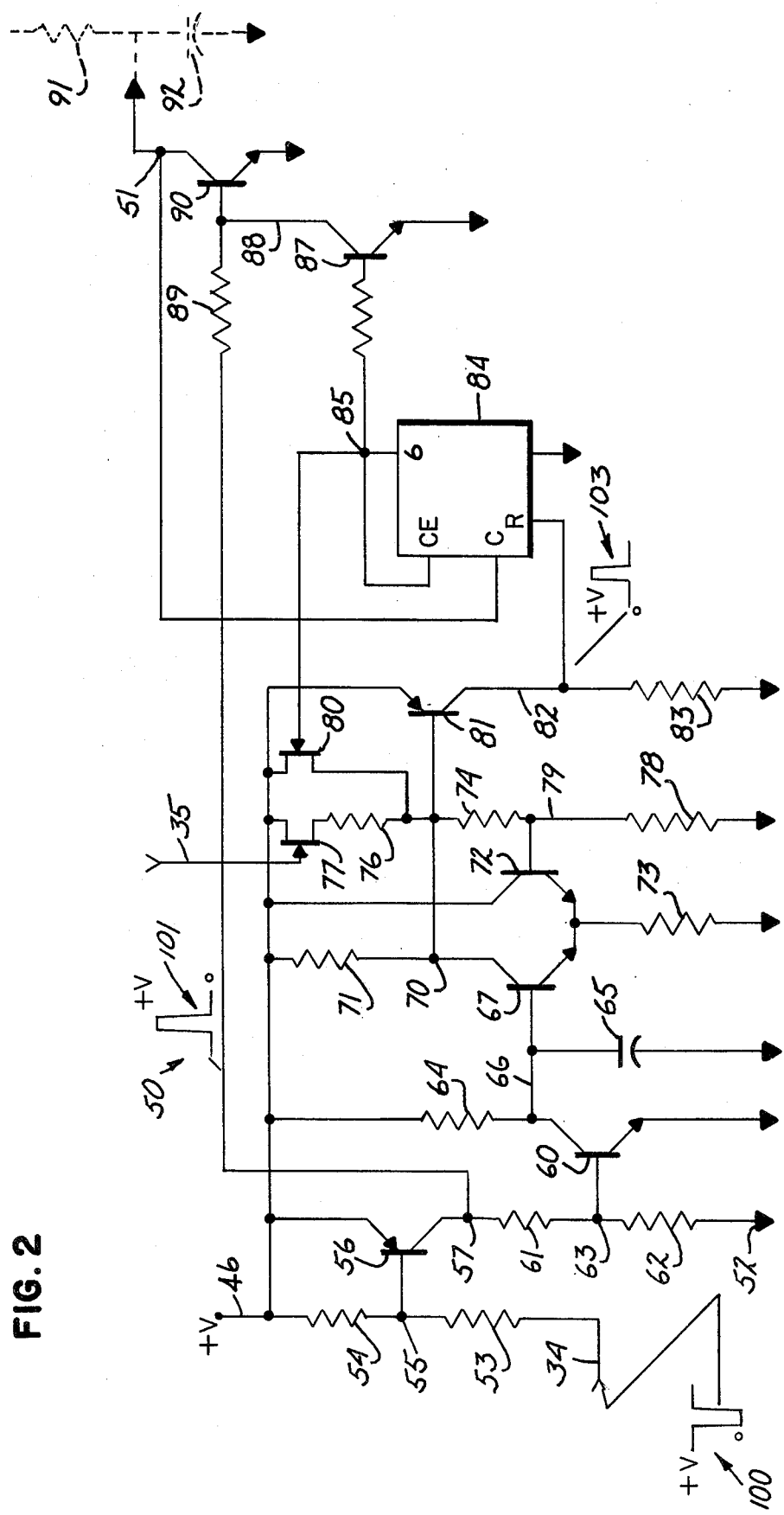
FIG. 2 is a schematic diagram of the tachycardia detector and control circuit of the pacemaker of FIG. 1.

Referring now to FIG. 2, the preferred circuit for control 50 of FIG. 1 is shown. The positive terminal of the battery connects to conductor 46 to energize the circuitry in the manner to be explained, and the negative terminal of the battery connects to the portions of the circuit indicated by the ground symbol 52.

The input to control 50 is received on conductor 34, and connects through series connected resistors 53 and 54 to the positive power supply conductor 46. The junction point of resistors 53 and 54 is designated by reference number 55, and this point connects to the base of a PNP transistor 56. The emitter of transistor 56 connects to a branch of the power supply conductor 46, and its collector connects to conductor 57 which connects through series connected resistors 61 and 62 to signal ground 52. The junction point 63 of these resistors connects to the base of an NPN transistor 60, whose emitter also connects to signal ground. An RC timing circuit comprising resistor 64 and capacitor 65 is connected between the positive power lead and signal ground, and the junction point of these components, designated by reference number 66, connects to the collector of transistor 60, and also to the base of transistor 67.

Transistor 67 is an NPN transistor having its collector connected by conductor 70 to resistor 71 which connects to the positive power supply. The emitter of transistor 67 is commonly connected with the emitter of another NPN transistor 72, and both emitters connect through resistor 73 to signal ground. The collector of transistor 72 connects to the positive power supply.

The base of transistor 72 connects to power supply conductor 46 through a series connection of resistors 74 and 76 and field effect transistor 77, and to ground through resistor 78. The gate of FET 77 is connected to lead 35 from the program controller. Another FET 80 is provided with its source and drain terminals connected in parallel with FET 77 and resistor 76, from conductor 46 to conductor 70.

A PNP transistor 81 has its emitter connected to conductor 46, and its base connected to conductor 70. The collector of transistor 81 connects via conductor 82 and resistor 83 to signal ground.

An integrated circuit counter, designated by reference number 84, is provided. The reset input connects to conductor 82, and the number 6 count output connects to conductor 85, a branch of which connects to the gate of FET 80, and another branch of which connects to the CE (clock enable) input of counter 84. A connection to the battery is also provided but is omitted from FIG. 2 for purposes of clarity.

Conductor 85 also connects through resistor 86 to the base of an NPN transistor 87. The emitter of this transistor connects to signal ground, and its collector connects via conductor 88 to the base of transistor 90. Conductor 57 also connects to the base of transistor 90 through resistor 89. NPN transistor 90 has its emitter connected to signal ground, and its collector connected to conductor 51. A branch of conductor 51 feeds back to the clock input of counter 84. Conductor 51 also extends, as shown in FIG. 1, to the reset inputs of oscillators 10 and 20. In the preferred embodiment, conductor 51 connects, preferably through further switching elements (not shown), to the junction point of timing resistors 91 and capacitors 92 as indicated in broken line in FIG. 2 for controlling the discharging and recharging thereof.

Operation of the pacemaker according to the present invention will now be explained with the aid of FIGS. 1 and 2. In normal operation the pacemaker operates as a conventional atrial-ventricular sequential demand type pacemaker. Upon occurrence of either a stimulating pulse or a spontaneous heart beat, both oscillators 10 and 20 are reset and begin to time out their predetermined programmed escape intervals. If a spontaneous heart beat occurs before the end of the escape interval, it is detected by filter 31 and is used to reset oscillators 10 and 20. If the spontaneous heart beat is not received before the end of the escape interval of the oscillators, indicating that the natural heart rate is too low or that natural heart signals are lacking, the atrial and ventricular oscillators fire in sequence to stimulate the upper and lower chambers of the heart. In this manner a minimum heart rate is established by the pacemaker, but if the spontaneous heart rate is fast enough the oscillators are continually reset and no stimulating pulses are delivered. As previously mentioned, in the preferred embodiment the escape interval and corresponding minimum beats per minute rate, and the time delay between the atrial and ventricular pulses can be controlled by program controller 40, although such control is not essential to the present invention.

The manner in which a detected heart signal is used to reset the oscillators is as follows. The signal picked up from the heart by the ventricular electrode is applied via terminals 23 and 24 and conductor 30 to filter 31 and amplifier 33. Assuming that amplifier 33 is energized, the occurrence of a beat is presented at lead 34 as a negative going pulse as indicated by waveform 100 in FIG. 2. In the absence of such a pulse, transistor 56 is off because the battery voltage +V is applied both to its emitter and base. Upon occurence of the pulse at lead 34, a voltage divider is established through resistors 54 and 53, causing a drop in voltage at the base and switching transistor 56 on. This in turn causes the voltage at conductor 57 to switch from ground potential to near the positive voltage supply to produce a positive going pulse as indicated by waveform 101. This pulse causes transistor 90 to switch on, pulling conductor 51 to ground. This rests the timing circuits for oscillators 10 and 20 as previously described.

The tachycardia detection and control features of the invention operate as follows. First of all, in a programmable pacemaker as shown in FIG. 1, tachycardia detection and control circuit 50 is enabled by providing a logical 1, or the plus battery voltage to conductor 35. As seen in FIG. 2, this turns on FET 77, thus completing the circuit path to the base of transistor 72. If the enabling signal at conductor 35 is absent, the tachycardia control function will be inhibited.

Upon occurrence of a pulse 100 and generation of the pulse 101 as previously described, transistor 60 is momentarily turned on due to a positive going pulse at conductor 63. When transistor 60 turns on, a discharge path is provided therethrough for discharging capacitor 65. At the end of the pulse, transistor 60 turns off, and capacitor 65 begins to recharge through resistor 64. The voltage at conductor 66, after being reset to zero, begins to charge on an exponential waveform until reset by transistor 60 on occurrence of the next input pulse at conductor 34. Resistor 64 and capacitor 65, in conjunction with a voltage sensing switch, form the basic timing components for tachycardia detection.

Transistors 67 and 72 and associated circuitry perform a voltage comparison and switching function. With FET 77 on as previously indicated, a current path is established through resistors 76, 74 and 78 to establish a voltage reference at conductor 79 which is connected to the base of transistor 72. With both transistors 67 and 72 off and beginning from a reset condition with substantially zero voltage at conductor 66, the voltage begins to increase as capacitor 65 charges. Unless this voltage is reset, it will eventually exceed the voltage at the base of transistor 72, causing transistor 67 to switch on. When this occurs, a voltage drop through load resistor 71 reduces the voltage at conductor 70 sufficiently to turn on transistor 81 to create a positive going output pulses at is collector on conductor 82 as indicated by waveform 103. However, if successive input pulses to conductor 34 occur at a rapid rate, the voltage at conductor 66 will be reset prior to reaching the voltage at conductor 79, and transistor 67 will remain off and no pulse at conductor 82 will be created. The resistors which establish the voltage reference at conductor 79 and the values of resistor 64 and capacitor 65 which determine the charging constant can be selected to provide the desired switching escape interval. In the preferred embodiment, the components are selected to switch transistor 67 if the escape interval between successive beats is 400 milliseconds or longer, corresponding to a heart beat of 150 beats per minute or less.

In normal demand pacing counter 84 is incremented with every detected heart beat. This is accomplished by feeding the output of transistor 90 via a branch of conductor 51 to the clock input of counter 84. The same pulse that increments counter 84 resets the voltage at capacitor 65 to zero and initiates a new charging cycle thereon. If the heart beat of the patient is in the normal range less than 150 beats per minute or whatever other limit may be set, the time constant will time out prior to being reset by the next heart beat, and a pulse will be delivered to conductor 82 as previously described to reset counter 84. Thus, in paced or spontaneous heart beating at a rate less than the predetermined rate, counter 84 is continually incremented to 1 and reset, and the count outputs higher than the first output, including count output number 6 shown in FIG. 2, remain at a logical zero state.

If successive heart beats occur separated by less than 400 milliseconds, capacitor 65 will be reset quickly enough that no reset pulse will be delivered to the counter so that the next heart beat will increment the counter to a count of 2. If the next beat returns to an escape interval greater than 400 milliseconds, indicating that the preceding beat was merely a premature beat, the counter will then be reset to zero. If a tachycardia rhythm is initiated, the occurrence of 5 successive pulses each within 400 milliseconds of the preceding pulses will increment counter 84 to a count of 6, producing a logical 1 at lead 85. At this point the control switches the pacemaker to an asychronous mode, although it will be appreciated that a lesser or greater number than 5 can be used by sensing from a different count output of the counter, if desired. The important point is that a single premature or extraneous beat or two will not initiate asynchronous operation. Upon reaching the count of 6, the logical 1 at conductor 85, which represents a voltage substantially near the positive battery voltage, turns on transistor 87 which in turn pulls the voltage at conductor 88 to substantially ground potential thus inhibiting transistor 90 from turning on. At the same time the voltage at conductor 85 is applied to the CE input of counter 84 to inhibit the counter from advancing in response to any further clock pulses. The voltage at conductor 85 also turns on FET 80 effectively bypassing resistor 76, to provide switching hysteresis as explained below.

With transistor 90 held in an off condition, and until counter 84 is reset, the atrial and ventricular oscillators 10 and 20 are prevented from being reset and therefore operate in a fixed rate, or asynchronous, mode. In this context, the term "asynchronous" refers to a lack of synchronization with heart beats, but it will be understood that the two oscillators remain synchronized with each other according to the predetermined time delay therebetween.

Asynchronous stimulation continues until the tachycardia cycle is broken. The circuit of FIG. 2 continues to monitor the escape interval and functions to reset counter 84 and bring the circuit back to normal demand operation if the sensed escape interval lengthens out to a predetermined value. However, it has been found advantageous to use a different, longer escape interval as the criterion for switching out of asynchronous mode as compared to the escape interval for originally switching into asynchronous mode. Thus, in the preferred embodiment, a series of escape intervals of less than 400 milliseconds causes switching into an asynchronous mode, but the circuit does not return to demand mode until a subsequent escape interval exceeds 650 milliseconds. This hysteresis effect is introduced to compensate for the refractory or insensitive period of the QRS amplifier following receipt of a pulse.

QRS amplifiers and filters typically have an insensitive period of roughly 190 to 320 milliseconds following the R-wave so as to blank out the circuit during the T-wave. In some pacemakers a special blanking circuit is provided, while in other cases the refractory period is provided by the naturally slow recovery time of the circuit due to the low bias current operating conditions thereof and filter characteristics which will not pass the T-wave. Either way, the blanking effect of the amplifier, if not compensated for by the introduction of hysteresis, can cause masking of pulses and premature reversion of the pacemaker to demand mode, even though the tachycardia cycle is not broken. To illustrate this problem, assume the following conditions. The pacemaker is operating in asynchronous mode, with pulses being emitted by the ventricular oscillator at 850 millisecond intervals, and the patient's heart beating in a tachycardia cycle with beats occurring at slightly less than 400 milliseconds (slightly greater than 150 beats per minute). Upon occurrence of an oscillator output, the QRS amplifier detects and passes that signal, and is then insensitive for the following assumed 200 millisecond period for a given amplifier. If a heart beat then occurs at approximately 180 milliseconds after the oscillator output pulse, the QRS wave of the beat will not be detected. A second heart beat somewhat less than 400 milliseconds later, or at somewhat less than 580 milliseconds following the last oscillator output will be detected and passed to control 50. In the above case, control 50 will have received the oscillator output pulses, followed some 580 milliseconds later by a detected heart beat. If the switching criterion for resuming normal operation were set at 400 milliseconds, the circuit of FIG. 2 would cause a change of modes, when in fact, in the example above, the tachycardia condition still exists with a heart rate of slightly more than 150 beats per minute.

To prevent this possibility, switching threshold hysteresis is introduced so that the escape interval for switching out of an asynchronous mode is set at the escape interval selected for detection of a tachycardia condition, plus the refractory or blanking time of the QRS amplifier or filter, plus a small guard band or safety margin. To simplify operation and minimize the amount of hysteresis required, it is preferable that the QRS amplifier used has a relatively short refractory period, preferably less than 200 milliseconds. The preferred embodiment uses an escape interval of approximately 650 milliseconds, which equals the 400 millisecond switching time, plus 190 milliseconds blanking time, pluse a guard band of approximately 60 milliseconds.

The hysteresis is achieved by turning on FET 80 at the time counter 84 reaches its 6 count and inhibits transistor 90 from delivering further resets. FET 80 shorts out resistor 76, thus changing the values of the voltage divider connected to the base of transistor 72, and in effect raising the voltage at conductor 79. This has the effect of requiring a longer escape interval before the charging of capacitor 65 will reach the new voltage reference to permit transistor 67 to turn on. When the longer escape interval is eventually reached, transistors 67 and 81 are turned on, delivering a reset pulse to counter 84 to reset it, and normal demand mode operation resumes until 5 more successive beats each having an escape interval of less than 400 milliseconds are encountered.

It is thus seen that the present invention provides tachycardia treatment by automatically switching a pacemaker from demand to asynchronous A-V sequential pacing upon establishment of a tachycardia rhythm by the heart, but not in response to merely a few premature or extraneous beats. A-V sequential pacing optimizes the probability of terminating the tachycardia in the quickest manner and minimizes electrode placement criticality. Switching hysteresis prevents premature return to demand mode due to masking of pulses.

What is claimed is:

1. A heart pacemaker for treatment of tachycardia comprising:

terminal means for connection to a patient's heart for delivering atrial and ventricular stimulation thereto;

generating means for delivering sequential atrial and ventricular electrical stimulation pulses to said terminal means at a predetermined repetition rate;

means for sensing the patient's heart beat and for providing signals in response thereto;

demand control means connected to said sensing means and operative in a demand mode for preventing delivery of said stimulating pulses if a heart beat occurs within a predetermined time interval following a preceding spontaneous or stimulated heart beat;

tachycardia detection and control means connected to receive signals from said sensing means and operatively connected for enabling said generating means to deliver said sequential atrial and ventricular electrical stimulation pulses in an asynchronous mode of operation in response to occurence of heart beats separated by a predetermined plurality of consecutive escape intervals of less than a predetermined duration; and means for determining said asychronous mode and returning control of delivering said pulses to said demand control when the escape interval between successive sensed beats exceeds a second predetermined duration which is larger than said first-mentioned predetermined duration.

2. A heart pacemaker according to claim 1 wherein said tachycardia detection and control means includes timing means, a counter, means for incrementing said counter on occurrence of a beat, means responsive to said timing means and operative to reset said counter if the escape interval between said beat and the succeeding beat exceeds said predetermined duration, and means for enabling said asynchronous mode on reaching a predetermined count by said counter.

3. A heart pacemaker according to claim 2, including switching hysteresis means operatively connected to said timing means for increasing said predetermined duration when said asynchronous mode is enabled, to prevent reset of said counter and returning from asynchronous mode until the sensed escape interval exceeds said increased duration, whereby to prevent premature return from asynchronous mode due to masking of pulses by the refractory period of the heart beat sensing means.

4. A heart pacemaker according to claim 1 further including programmable means connected to said tachycardia detection and control means for selective enablement or disablement thereof.

5. A heart pacemaker according to claim 1 further including a magnetically operated switch operatively connected to enable said asynchronous mode of operation when activated by an externally applied magnetic field.

6. A heart pacemaker for treatment of tachycardia comprising:

terminal means for connection to a patient's heart for delivering atrial and ventricular stimulation thereto;

generating means for delivering sequential atrial and ventricular electrical stimulation pulses to said terminal means at a predetermined repetition rate;

means for sensing the patient's heart beat and for providing signals in response thereto;

tachycardia detection and control means connected to receive signals form said sensing means and operatively connected for enabling said generating means for deliver said sequential atrial and ventricular electrical stimulation pulses in an asynchronous mode of operation in response to occurence of heart beats separated by a predetermined plurality of consecutive escape intervals of less than a predetermined duration and, means for terminating said asynchronous mode when the escape interval between successive sensed beats exceeds a second predetermined duration which is larger than said first-mentioned predetermined duration.

* * * * *

UNITED STATES PATENT AND TRADEMARK OFFICE
CERTIFICATE OF CORRECTION

PATENT NO. : 4,421,114

DATED : Dec. 20, 1983

INVENTOR(S) : Barouh V. Berkovitz and Ray S. McDonald

It is certified that error appears in the above-identified patent and that said Letters Patent is hereby corrected as shown below:

Column 1, line 25, "best" should be --beat--;
Column 2, line 12, "stimulations pulse" should be --stimulation pulses--;
Column 2, line 62 "ventrical" should be --ventricle--;
Column 5, line 30 "occurence" should be --occurrence--;
Column 6, line 8, "pulses" should be --pulse--;
Column 6, line 8, "is" should be --its--;
Column 8, line 9, "pluse" should be --pulse--;
Column 8, line 59, "occurence" should be --occurrence--;
Column 8, line 63, "determining" should be --terminating--;

UNITED STATES PATENT AND TRADEMARK OFFICE
CERTIFICATE OF CORRECTION

PATENT NO. : 4,421,114                         Page 2 of 2

DATED : Dec. 20, 1983

INVENTOR(S) : Barouh V. Berkovits and Ray S. McDonald

It is certified that error appears in the above-identified patent and that said Letters Patent is hereby corrected as shown below:

Column 8, line 63, "asychronous" should be --asynchronous--;

Column 10, line 14, "form" should be --from--;

Column 10, line 18, "occurence" should be --occurrence--.

On the face of the patent, the following should be added:

[73] Assignee: Medtronic, Inc., Minneapolis, Minnesota, a Minnesota corporation

Signed and Sealed this

Seventeenth Day of July 1984

[SEAL]

*Attest:*

GERALD J. MOSSINGHOFF

*Attesting Officer*           *Commissioner of Patents and Trademarks*